United States Patent
Kanemaru et al.

(10) Patent No.: US 12,419,820 B2
(45) Date of Patent: Sep. 23, 2025

(54) FATTY ACID CALCIUM SALT PARTICLES AND COSMETICS

(71) Applicant: NOF CORPORATION, Tokyo (JP)

(72) Inventors: Tetsuya Kanemaru, Tokyo (JP); Yoshihiro Nishiyama, Tokyo (JP); Takuya Hiruma, Tokyo (JP); Yuka Iwahashi, Tokyo (JP); Takeshi Yoshimura, Hyogo (JP); Mako Iwasaki, Hyogo (JP)

(73) Assignee: NOF CORPORATION, Tokyo (JP)

( * ) Notice: Subject to any disclaimer, the term of this patent is extended or adjusted under 35 U.S.C. 154(b) by 492 days.

(21) Appl. No.: 17/796,092

(22) PCT Filed: Feb. 17, 2021

(86) PCT No.: PCT/JP2021/006009
§ 371 (c)(1),
(2) Date: Jul. 28, 2022

(87) PCT Pub. No.: WO2021/172146
PCT Pub. Date: Sep. 2, 2021

(65) Prior Publication Data
US 2023/0077466 A1  Mar. 16, 2023

(30) Foreign Application Priority Data
Feb. 28, 2020 (JP) ................................ 2020-033890

(51) Int. Cl.
*A61K 8/36* (2006.01)
*A61Q 19/10* (2006.01)

(52) U.S. Cl.
CPC ............. *A61K 8/36* (2013.01); *A61Q 19/10* (2013.01); *A61K 2800/412* (2013.01)

(58) Field of Classification Search
CPC .. A61K 8/36; A61K 2800/412; A61K 8/0241; A61K 8/361; A61Q 19/10; A61Q 1/10; C07C 51/412; C07C 53/126
See application file for complete search history.

(56) References Cited

U.S. PATENT DOCUMENTS

| 5,093,099 A * | 3/1992 | Haishi ........................ A61Q 1/02 424/641 |
| 6,160,142 A * | 12/2000 | Sawada .................. C07C 51/412 554/158 |
| 2016/0143824 A1 * | 5/2016 | Niimi ......................... A61Q 1/02 424/692 |
| 2018/0093938 A1 * | 4/2018 | Yoshimura ............... A61Q 1/12 |

FOREIGN PATENT DOCUMENTS

| JP | 2000-169342 A | 6/2000 |
| JP | 2007-186463 A | 7/2007 |
| JP | 2018-168145 A | 11/2018 |
| WO | WO-2016/132967 A1 | 8/2016 |

OTHER PUBLICATIONS

Sawada et. al. "Preparation of sub-micron particles of fatty acid multivalent metal salt using newly developed jet-mixing method" J Soc Powder Tech. 2003, 40, 8, 11-18. (Year: 2003).*
Sawada et. al.—machine translation. "Preparation of sub-micron particles of fatty acid multivalent metal salt using newly developed jet-mixing method" J Soc Powder Tech. 2003, 40, 8, 11-18. (Year: 2003).*
Sawada et al. "Characterization of fine metallic soap particles by X-ray diffraction, differential scanning calorimetry, and specific surface area analysis." J Oleo Sci 2004, 53, 12, 627-640. (Year: 2004).*
International Searching Authority, "International Search Report," issued in connection with International Patent Application No. PCT/JP2021/006009, dated Apr. 13, 2021.
International Searching Authority, "Written Opinion," issued in connection with International Patent Application No. PCT/JP2021/006009, dated Apr. 13, 2021.

* cited by examiner

*Primary Examiner* — Ali Soroush
*Assistant Examiner* — Rajan Pragani
(74) *Attorney, Agent, or Firm* — Foley & Lardner LLP

(57) ABSTRACT

The invention relates to particles of a calcium salt of a fatty acid having 12 to 22 carbon atoms, wherein the median size is 4.0 μm to 15.0 μm, the particle size digest A expressed by the following equation (1) satisfies the relation A≤2.0, and the average thickness is 350 to 800 nm.

Particle size digest $A=(D90-D10)/D50$   equation (1)

(Here, $4.0 \leq D50 \leq 15.0$.)
D10: the 10% cumulative size (μm) of the fatty acid calcium salt particles on a volumetric basis
D50: the median size (μm) of the fatty acid calcium salt particles on a volumetric basis
D90: the 90% cumulative size (μm) of the fatty acid calcium salt particles on a volumetric basis

5 Claims, 1 Drawing Sheet

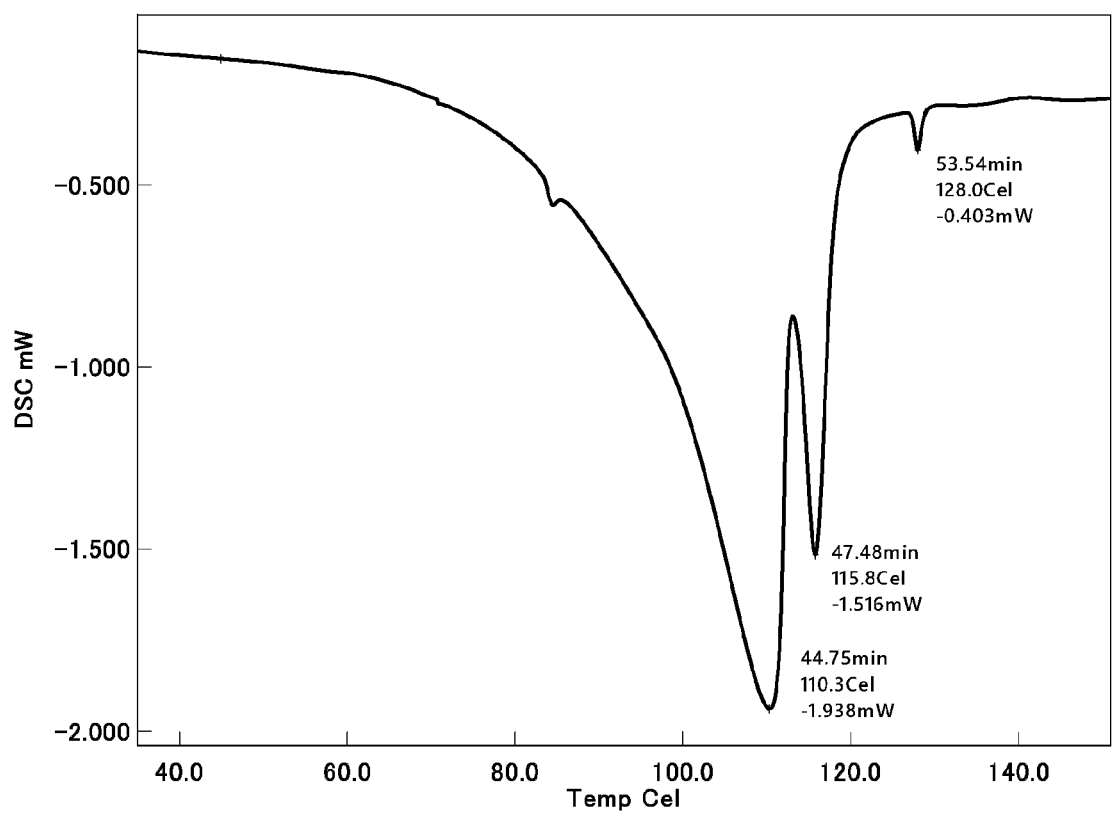

FATTY ACID CALCIUM SALT PARTICLES AND COSMETICS

CROSS-REFERENCE TO RELATED APPLICATIONS

The present application claims priority under 37 U.S.C. § 371 to International Patent Application No. PCT/JP2021/006009, filed Feb. 17, 2021, which claims priority to and the benefit of Japanese Patent Application No. 2020-033890, filed on Feb. 28, 2020. The contents of these applications are hereby incorporated by reference in their entireties.

TECHNICAL FIELD

The present invention relates to novel fatty acid calcium salt particles and a cosmetic containing the fatty acid calcium salt particles.

BACKGROUND ART

A fatty acid calcium salt is a metallic soap which is useful as a cosmetic additive and has been used for the purpose of improving the smoothness or the adhesion on the skin or as a dispersing agent for pigments or another purpose.

Patent Literature 1 describes a metallic soap which is a calcium salt or the like of a fatty acid having 6 to 24 carbon atoms obtained by a metathesis method and in which the pH is not in the alkaline range when the metallic soap is dispersed in water.

Patent Literature 2 discloses that a solid powder cosmetic having excellent use feeling, formability and impact resistance is obtained when metallic soap microparticles having a specific particle size are combined with a partially cross-linked organopolysiloxane polymer.

Patent Literature 3 discloses that a solid powder cosmetic having excellent formability, impact resistance, durability and the like is obtained when a specific amount of metallic soap microparticles having a specific particle size distribution are used.

CITATION LIST

Patent Literature

Patent Literature 1: JP-A-2007-186463
Patent Literature 2: JP-A-2018-168145
Patent Literature 3: JP-A-2000-169342

SUMMARY OF INVENTION

Technical Problem

The conventional metallic soaps, however, have room for improvement in terms of the use feeling.

A purpose of the invention is to provide a novel metallic soap and a cosmetic which have excellent use feeling.

Solution to Problem

As a result of intensive investigation to solve the problem, the inventors have found that fatty acid calcium salt particles having a particle size, a particle size digest and a thickness within specific ranges have excellent use feeling.

That is, the invention relates to the fatty acid calcium salt particles and the cosmetic below.

[1] Particles of a calcium salt of a fatty acid having 12 to 22 carbon atoms, wherein the median size is 4.0 to 15.0 μm, the particle size digest A expressed by the following equation (1) satisfies the relation A≤2.0, and the average thickness is 350 to 800 nm.

$$\text{Particle size digest } A=(D90-D10)/D50 \quad \text{equation (1)}$$

(Here, $4.0 \leq D50 \leq 15.0$.)
D10: the 10% cumulative size (μm) of the fatty acid calcium salt particles on a volumetric basis
D50: the median size (μm) of the fatty acid calcium salt particles on a volumetric basis
D90: the 90% cumulative size (μm) of the fatty acid calcium salt particles on a volumetric basis

[2] The fatty acid calcium salt particles described in [1], wherein the fatty acid having 12 to 22 carbon atoms is myristic acid.

[3] A cosmetic containing the fatty acid calcium salt particles described in [1] or [2].

Advantageous Effects of Invention

According to the invention, fatty acid calcium salt particles having excellent use feeling can be provided.

Moreover, according to the invention, a cosmetic having excellent use feeling can be provided because the fatty acid calcium salt particles are contained.

BRIEF DESCRIPTION OF DRAWINGS

The FIGURE is a FIGURE showing the heat absorption graph of calcium myristate by differential thermal analysis (DSC).

DESCRIPTION OF EMBODIMENTS

The invention is explained in further detail below.

The fatty acid calcium salt particles of the invention are composed of a calcium salt of a divalent fatty acid having 12 to 22 carbon atoms. The particles can be prepared by a metathesis method in which a fatty acid-alkaline compound salt obtained by reacting a monovalent alkaline compound with a fatty acid having 12 to 22 carbon atoms and a divalent calcium salt are reacted in an aqueous solution.

The fatty acid used as the raw material of the fatty acid-alkaline compound salt is not particularly restricted as long as the fatty acid has 12 to 22 carbon atoms. That is, the fatty acid may be a naturally derived fatty acid or a synthetic fatty acid, may be a saturated fatty acid or an unsaturated fatty acid and may be a linear or branched fatty acid. The fatty acid may contain a functional group such as a hydroxyl group, an aldehyde group and an epoxy group in its structure. The fatty acid is preferably a linear saturated fatty acid.

The fatty acid has 12 or more carbon atoms and thus can give excellent use feeling to the cosmetic. Because the number of the carbon atoms is 22 or less, the fatty acid is industrially easily obtained, and the solubility of the obtained fatty acid-alkaline compound salt in water does not decrease significantly. Thus, the productivity is high. The number of the carbon atoms of the fatty acid is preferably 12 to 18, more preferably 14 (which means that the fatty acid calcium salt is calcium myristate).

Examples of the fatty acid include lauric acid, myristic acid, myristoleic acid, palmitic acid, palmitoleic acid, stearic acid, oleic acid, linoleic acid, arachic acid, behenic acid, erucic acid, hydroxystearic acid, epoxystearic acid and the like. Of these, myristic acid is preferable. When a mixed fatty acid is used, the myristic acid content of the fatty acid is preferably 50% or more, more preferably 60% or more, further preferably 70% or more.

The monovalent alkaline compound used as the raw material of the fatty acid-alkaline compound salt is a hydroxide of an alkali metal (sodium, potassium or the like), ammonia, an amine such as monoethanolamine, diethanolamine and triethanolamine or the like. Because the solubility of the resulting fatty acid-alkaline compound salt in water is high, a hydroxide of an alkali metal such as sodium and potassium is preferable.

The fatty acid-alkaline compound salt used in the invention is obtained by reacting the monovalent alkaline compound and the fatty acid generally at a temperature which is the melting point of the fatty acid or higher and at which the fatty acid does not decompose, preferably at 100° C. or lower, more preferably at 50 to 100° C., further preferably at 60 to 95° C., particularly preferably at 70 to 95° C.

The fatty acid calcium salt particles of the invention can be obtained, for example, by reacting the fatty acid-alkaline compound salt obtained above and a calcium salt in an aqueous solution. The calcium salt is specifically a salt of inorganic calcium and an inorganic acid or an organic acid. Examples of the calcium salt include calcium chloride, calcium acetate and the like. In particular, chloride of calcium is preferable because of the high solubility in water and the efficient reaction with the fatty acid-alkaline compound salt.

The reaction of the fatty acid-alkaline compound salt and the divalent calcium salt is conducted specifically by preparing a calcium salt-containing aqueous solution and a fatty acid-alkaline compound salt-containing aqueous solution separately and then mixing the solutions. For example, the reaction is conducted by adding the calcium salt-containing aqueous solution to the fatty acid-alkaline compound salt-containing aqueous solution or adding the both into a separate reaction bath.

Regarding mixing of the fatty acid-alkaline compound salt-containing aqueous solution and the calcium salt-containing aqueous solution, when the calcium salt-containing aqueous solution is fed into the fatty acid-alkaline compound salt-containing aqueous solution at once, for example, the shapes of the obtained fatty acid calcium salt particles may become ununiform, and the particle size distribution may become broad. Thus, in the invention, the calcium salt-containing aqueous solution is preferably dropped gradually at an appropriate speed to the fatty acid-alkaline compound salt-containing aqueous solution.

The concentration of the fatty acid-alkaline compound salt during the production of the fatty acid calcium salt is generally 1 mass % to 20 mass %, preferably 5 mass % to 15 mass % in view of the productivity of the fatty acid calcium salt and in view of the handling property of the fatty acid-alkaline compound salt-containing aqueous solution or the obtained fatty acid calcium salt slurry. The concentration of the fatty acid-alkaline compound salt is preferably 1 mass % or more because the productivity of the fatty acid calcium salt is excellent. When the concentration is 20 mass % or less, the viscosity of the fatty acid-alkaline compound salt-containing aqueous solution or the obtained fatty acid calcium salt slurry does not increase, and uniform reaction is possible. Here, the concentration of the calcium salt in the calcium salt-containing liquid is generally 10 mass % to 50 mass %, preferably 10 mass % to 40 mass % in view of the productivity of the fatty acid calcium salt and in view of the handling property of the fatty acid-alkaline compound salt-containing aqueous solution or the obtained fatty acid calcium salt slurry.

The reaction of the fatty acid-alkaline compound salt and the calcium salt is conducted under the temperature conditions which one skilled in the art generally uses considering the solubility of the fatty acid-alkaline compound salt. The temperature is preferably 50 to 100° C., more preferably 60 to 95° C. When the reaction temperature is 50° C. or higher, the reaction rate of the fatty acid-alkaline compound salt and the calcium salt is excellent.

For the purpose of stabilizing the fatty acid calcium salt slurry and improving the productivity of the fatty acid calcium salt during the reaction of the fatty acid-alkaline compound salt and the calcium salt, a polyalkylene glycol ether, especially a triblock ether having a structure in which an oxypropylene block is between oxyethylene blocks (EO-PO-EO), is preferably contained in the fatty acid calcium salt slurry. The polyalkylene glycol ether content of the fatty acid calcium salt slurry is generally 0.01 parts by mass to 5 parts by mass, preferably 0.05 parts by mass to 2 parts by mass based on 100 parts by mass of the fatty acid-alkaline compound salt. The polyalkylene glycol ether may be contained in the reaction system before the reaction of the monovalent alkaline compound and the fatty acid and may also be contained in the reaction system before the reaction of the fatty acid-alkaline compound salt and the calcium salt.

A fatty acid calcium salt cake with a water content that is reduced through separation with one dehydrator, a filter press or the like is obtained by the method. The fatty acid calcium salt cake with a reduced water content is dried with a rotary dryer, a flash dryer, a ventilated tray dryer, a spray dryer, a fluidized bed dryer or the like.

In the invention, it is necessary that the fatty acid calcium salt cake is dried at $(\alpha-40)$ ° C.$\leq\alpha\leq(\alpha+5°$ C.) regarding the contained water evaporation peak top temperature ($\alpha°$ C.) of the produced fatty acid calcium salt. Here, the contained water evaporation peak top temperature is the top peak of the peak in the temperature range in which the residual water contained in the fatty acid calcium salt which cannot be removed by the drying starts to desorb, and for example, the contained water evaporation peak top temperature is 110.3° C. in the heat absorption graph of calcium myristate by differential thermal analysis (DSC) in the FIGURE. The specific drying temperature differs with the kind of the obtained fatty acid calcium salt but is 115° C. or lower in the case of calcium myristate, for example. When the drying treatment is conducted at a temperature higher than 115° C., the microparticles adhere to each other, and the particle thickness is apt to be large. On the other hand, when the drying treatment is conducted at a temperature lower than 70° C., the drying property decreases, and a large amount of water remains in the compound.

The fatty acid calcium salt particles of the invention have a narrow particle size distribution and thus can uniformly exist in the cosmetic, and the effects of action of the invention (especially the improvement of the texture of the cosmetic) are exhibited more stably. Specifically, the particle size digest A of the fatty acid calcium salt particles expressed by the following equation (1) is 2.0 or less.

Particle size digest $A=(D90-D10)/D50$    equation (1)

(Here, $4.0\leq D50\leq 15.0$.)

D10: the 10% cumulative size (μm) of the fatty acid calcium salt particles on a volumetric basis D50: the median size (μm) of the fatty acid calcium salt particles on a volumetric basis D90: the 90% cumulative size (μm) of the fatty acid calcium salt particles on a volumetric basis In the invention, the particle size digest A is calculated from the particle sizes measured by the Microtrac laser diffraction method. When the particle size digest A is 2.0 or less, the fatty acid calcium salt particles in the cosmetic have a uniform particle size, and the dispersibility of the cosmetic is excellent. Moreover, the productivity does not decrease, and a cosmetic having an aimed texture can be produced. The particle size digest A more preferably satisfies the relation $0.5 \le A \le 1.8$. When the relation $0.5 \le A \le 1.8$ is satisfied, the effects of action of the invention are obtained further more stably. When the particle size digest A is 0.5 or more, the yield does not decrease, and industrially stable production is possible.

Here, when a cumulative curve is drawn in which the total volume of the powder population is regarded as 100% in the equation (1), the particle sizes at 10%, 50% and 90% of the cumulative curve are referred to as the 10% cumulative size (D10), the 50% median size (D50; median size) and the 90% cumulative size (D90) (μm), respectively.

The particle size digest A can be adjusted by appropriately adjusting the concentration of the fatty acid-alkaline compound salt, the temperature of the reaction of the fatty acid-alkaline compound salt and the calcium salt and the dropping speed for dropping the calcium salt-containing aqueous solution to the fatty acid-alkaline compound salt-containing aqueous solution. Moreover, when the particles have a broad particle size distribution, namely, a large particle size digest A value, the particle size digest A can be adjusted through sorting using a sieve such as 100 mesh, 200 mesh and 330 mesh in the posttreatment.

The Microtrac laser diffraction method used here is a method for determining the particle size distribution using scattered light obtained by irradiating particles with laser beam. In the invention, the measurement is made by the wet method in which the sample is directly fed while an organic solvent into which the fatty acid calcium salt particles do not dissolve, such as organic solvents including ethanol, isopropyl alcohol and the like, circulates. Moreover, the measurement target in the invention has a particle size in the range of 0.1 μm to 200 μm, and the value expressed by the equation (1) is the particle size digest A. In the invention, the measurement can be made, for example, using Microtrac MT-3000 manufactured by Nikkiso Co., Ltd.

The median size (D50) of the fatty acid calcium salt particles of the invention on a volumetric basis is 4.0 to 15.0 μm. Due to the particle size, the texture upon use is excellent. The median size of the fatty acid calcium salt particles is preferably 5.0 to 12.0 μm, more preferably 6.0 to 10.0 μm. The particle size can be measured by the Microtrac laser diffraction method like the particle size digest A described above.

The average particle thickness of the fatty acid calcium salt particles of the invention is 350 to 800 nm. Due to the thickness, the particles easily dissolve even under mild mixing conditions (production method) for the cosmetic. Moreover, the cosmetic is easily applied to the skin evenly, and the texture after the application can also be improved. When the average thickness is 350 nm or more, the handling property of the fatty acid calcium salt particles during the addition to the cosmetic is excellent, and there is no risk of reduction in the workability. The average particle thickness is more preferably 400 to 700 nm. When the average thickness of 400 to 700 nm is satisfied, the effects of action of the invention are obtained further more stably.

The thickness of a particle is the value of the length of the side face of a fatty acid calcium salt particle when the face with the largest area is regarded as the front face.

In order to obtain fatty acid calcium salt particles having the specific thickness, the calcium salt-containing aqueous solution is preferably dropped gradually into the fatty acid-alkaline compound salt-containing aqueous solution when the calcium salt-containing aqueous solution and the fatty acid-alkaline compound salt-containing aqueous solution, which are prepared separately by metathesis reaction, are mixed. The dropping speed is preferably 0.005 to 0.8 mol/mol per unit time, further preferably 0.01 to 0.5 mol/mol. By mixing at the dropping speed, the exchange reaction of the alkali and the calcium can be advanced gently, and fatty acid calcium salt particles having a moderate thickness can be obtained. When the speed is 0.005 mol/mol or more, the particle thickness does not become small, and fatty acid calcium salt particles having a desired thickness can be obtained. On the other hand, when the dropping speed per unit time is 0.8 mol/mol or less, the fatty acid calcium salt particles have a uniform shape, and the particles have a desired thickness. Thus, the particle size is not uneven, which is excellent.

The unit of the calcium salt dropped, "mol/mol", is the number of moles of the calcium salt dropped per 1 mole of the fatty acid-alkaline compound.

The shape of the fatty acid calcium salt particles of the invention is not particularly limited but is preferably plate.

The cosmetics for which the fatty acid calcium salt particles of the invention can be used include skin care cosmetics such as facial washing cream, face lotion, massage cream, milky lotion and moisture cream, makeup cosmetics such as foundation, eye shadow, eye liner, lipsticks and blush, body care cosmetics such as bath products, sunscreen creams and deodorant spray, hair care cosmetics such as shampoo, conditioner, hair liquids and hair dyes and the like.

In addition to the fatty acid calcium salt particles of the invention, as other known cosmetic materials, organic pigments, inorganic pigments, fragrance, oils and fats, waxes, hydrocarbons, higher fatty acids, higher alcohols, esters, silicone oils, nonionic, anionic, cationic and amphoteric surfactants, other surfactants, moisturizing agents, ultraviolet absorbers, antioxidants and the like can be used.

EXAMPLES

The invention is explained further specifically below referring to Examples and Comparative Examples.

[Preparation of Fatty Acid Calcium Salt Particles]

Example 1

Into a 3-L separable flask, 250 g of myristic acid (NAA-142 manufactured by NOF Corporation), 1.25 g of polyethylene glycol/polypropylene glycol block ether (manufactured by NOF Corporation, product name: Plonon 104) and 2500 g of water were charged, and the temperature was increased to 90° C. Next, 87.0 g of 48 mass % aqueous sodium hydroxide solution was added and stirred at the same temperature (90° C.) for an hour, and thus an aqueous sodium myristate solution was obtained. Then, while maintaining at 90° C., 174.5 g of 35 mass % aqueous calcium chloride solution was dropped to the aqueous sodium myristate solution over 30 minutes [dropping speed: 0.39 (mol/mol)]. After the completion of dropping, the mixture was maintained at 90° C. and stirred for 10 minutes for aging. Water in an amount of 1500 g was added to the obtained aqueous mixed fatty acid calcium salt solution slurry, and the mixture was cooled to 65° C. or lower. Then, the mixture was filtered with a suction filter, followed by washing twice with 1000 g of water, and the obtained cake was dried at 80° C. using a ventilated tray dryer and crushed in a mill. Thus, calcium myristate particles were obtained.

Example 2

Into a 3-L separable flask, 250 g of myristic acid (NAA-142 manufactured by NOF Corporation), 1.25 g of polyethylene glycol/polypropylene glycol block ether (manufactured by NOF Corporation, product name: Plonon 104) and 2500 g of water were charged, and the temperature was increased to 80° C. Next, 87.0 g of 48 mass % aqueous sodium hydroxide solution was added and stirred at the same temperature (90° C.) for an hour, and thus an aqueous sodium myristate solution was obtained. Then, while maintaining at 80° C., 174.5 g of 35 mass % aqueous calcium chloride solution was dropped to the aqueous sodium myristate solution over 40 minutes [dropping speed: 0.29 (mol/mol)]. After the completion of dropping, the mixture was maintained at 80° C. and stirred for 10 minutes for aging. Water in an amount of 1500 g was added to the obtained aqueous mixed fatty acid calcium salt solution slurry, and the mixture was cooled to 65° C. or lower. Then, the mixture was filtered with a suction filter, followed by washing twice with 1000 g of water, and the obtained cake was dried at 107° C. using a flash dryer and crushed in a mill. Thus, calcium myristate particles were obtained.

Example 3

Into a 3-L separable flask, 250 g of myristic acid (NAA-142 manufactured by NOF Corporation) and 2500 g of water were charged, and the temperature was increased to 80° C. Next, 87.0 g of 48 mass % aqueous sodium hydroxide solution was added and stirred at the same temperature (90° C.) for an hour, and thus an aqueous fatty acid-alkaline compound salt solution was obtained. Then, while maintaining at 80° C., the aqueous sodium myristate solution was dropped to 174.5 g of 35 mass % aqueous calcium chloride solution over 30 minutes [dropping speed: 0.39 (mol/mol)]. After the completion of dropping, the mixture was maintained at 80° C. and stirred for 10 minutes for aging. Water in an amount of 1500 g was added to the obtained aqueous mixed fatty acid calcium salt solution slurry, and the mixture was cooled to 65° C. or lower. Then, the mixture was filtered with a suction filter, followed by washing twice with 1000 g of water, and the obtained cake was dried at 100° C. using a flash dryer and crushed in a mill. Thus, calcium myristate particles were obtained.

Comparative Example 1

Into a 5-L glass flask, 250 g of myristic acid (NAA-142 manufactured by NOF Corporation) and 3000 g of water were charged, and the temperature was increased to 80° C. under stirring. Next, 43 g of calcium hydroxide was added at the same temperature over 30 minutes. After the completion, the temperature was increased to 90° C., and stirring was continued for an hour. Thus, a calcium myristate slurry was obtained. The calcium myristate slurry was cooled to 60° C. and then filtered using a suction filter, and then the obtained cake was dried at 80° C. using a ventilated tray dryer and pulverized in a mill. Thus, calcium myristate particles were obtained.

Comparative Example 2

Two 5-L stainless steel beakers were prepared. An aqueous solution containing 5.0 mass % sodium myristate in an amount of 4500 g was charged into one of the beakers, and 4500 g of an aqueous solution containing 2.3 mass % calcium chloride was charged into the other. Both were adjusted to 85° C. The two aqueous solutions were mixed together at once in a 15-L stainless steel beaker, stirred for a minute and then filtered using a suction filter, followed by washing twice with 1000 g of water, and the obtained cake was dried at 120° C. using a flash dryer and pulverized in a mill. Thus, calcium myristate particles were obtained.

The median sizes, the particle size digests A [values each calculated from the 10% cumulative size D10 (μm) on a volumetric basis, the median size D50 (μm) on a volumetric basis and the 90% cumulative size D90 (μm) on a volumetric basis] and the particle thicknesses of the calcium myristate particles of Examples 1 to 3 and Comparative Examples 1 and 2 were measured using the following devices by the methods described above. The results are shown in Table 1.

(1) Particle Size Digest A and Median Size

A sample in an amount of 2.0 g was taken in a 100-ml glass beaker, and 3 to 5 ml of a nonionic surfactant (example; Nonion NS-210 manufactured by NOF Corporation) was dropped and blended with a spatula. Next, 20 ml of purified water was added, and the sample was dispersed by ultrasonic wave. The volume was adjusted to 100 ml, and thus a measurement sample was obtained. The sample was fed to and measured with a particle size distribution analyzer (machine name "Microtrac MT-3000" manufactured by Nikkiso Co., Ltd.) (principle: laser diffraction/scattering method).

A cumulative curve was drawn in which the total volume of the powder population measured was regarded as 100%, and the particle sizes at 10%, 50% and 90% of the cumulative curve were determined as the 10% size (D10), the 50% size (D50; median size) and the 90% size (D90) (μm), respectively. The particle size digest A was determined from the obtained D10, D50 and D90.

(2) Particle Thickness

The particle thickness was measured by the following method using a scanning electron microscope. A sample obtained by adhering fatty acid calcium salt particles on a double-sided carbon tape and then coating the particle surfaces with platinum particles by vapor deposition was observed at an acceleration voltage of 1.0 kV and at 2000× magnification, and the thicknesses of particles were measured at random. The average values of the results of measurement of thicknesses of 10 particles at random are shown in Table 1.

[Assessment of Use Feeling]

The textures upon use and the like of the fatty acid calcium salt particles obtained by the invention were assessed based on the following criteria. The results are shown in Table 1.

(Smoothness)

Two expert analysts determined the smoothness of the fatty acid calcium salt particles when the particles were applied to the skin as follows, and the smoothness was determined to be excellent in the case of B or A.

A: very smooth
B: smooth
C: not so smooth (Adhesion)

Two expert analysts determined the adhesion to the skin of the fatty acid calcium salt particles when the particles were applied to the skin as follows, and the application to the skin (adhesion) was determined to be excellent in the case of B or A.

A: very high adhesion
B: high adhesion
C: slightly low adhesion (Transparency)

Two expert analysts determined the transparency of the fatty acid calcium salt particles when the particles were applied to the skin as follows, and the transparency was determined to be excellent in the case of B or A.

A: very high transparency
B: high transparency
C: slightly low transparency
D: low transparency

TABLE 1

| | D10 (μm) | D50 (median size) (μm) | D90 (μm) | Particle Size Digest A | Particle Thickness (nm) | Smoothness | Adhesion | Transparency |
|---|---|---|---|---|---|---|---|---|
| Example 1 | 4.1 | 6.7 | 11.0 | 1.0 | 596 | B | B | B |
| Example 2 | 3.9 | 6.1 | 9.5 | 0.9 | 562 | A | B | B |
| Example 3 | 2.9 | 4.3 | 6.5 | 0.8 | 480 | B | A | A |
| Comparative Example 1 | 3.3 | 16.2 | 50.4 | 2.9 | 1240 | C | C | C |
| Comparative Example 2 | 0.4 | 1.1 | 3.2 | 2.5 | 152 | C | B | D |

As shown in Table 1, the results of the fatty acid calcium salt particles of Examples 1 to 3, in which the median sizes, the particle size digests and the particle thicknesses were in specific ranges, were excellent in all the items of smoothness, adhesion and transparency, and it is seen that the fatty acid calcium salt particles had excellent use feeling. On the other hand, the results of the fatty acid calcium salt particles of Comparative Examples 1 and 2, in which the median sizes, the particle size digests and the particle thicknesses did not satisfy the specific ranges, did not meet the criteria in some of the items of smoothness, adhesion and transparency.

FORMULATION EXAMPLES: EYE SHADOW

Formulation examples of eye shadow containing the fatty acid calcium salt particles of the invention are shown in Table 2 below.

TABLE 2

| Components | Formulation Example 1 (mass %) | Formulation Example 2 (mass %) |
|---|---|---|
| Talc | 20 | — |
| Mica | 12 | 6 |
| Sericite | 7 | — |
| Silicic Anhydride | 4 | 4 |
| Calcium Myristate (Example 1) | 4 | 4 |
| Iron Oxide Red | 5 | — |
| Iron Oxide Yellow | 5 | — |
| Iron Oxide Black | 2 | — |
| Red Iron Oxide-Coated Titanium Mica (Timica Golden Bronze) | 3 | — |
| Titanium Mica (Timiron SuperGold) | 14 | — |
| Titanium Mica (Timiron Soft Luster White 6500) | 8 | — |
| Titanium Oxide-Coated Borosilicate Glass (Metashine MT1080RS) | — | 70 |
| Vaseline | 2 | 2 |
| Diisostearyl Malate | 7 | 7 |
| Glycerol Tri 2-Ethylhexanoate | 2 | 2 |
| Antioxidant | Adequate Amount | Adequate Amount |
| Preservative | Adequate Amount | Adequate Amount |

Although the invention has been explained in detail referring to specific embodiments, it is obvious to one skilled in the art that various changes and modifications can be made without departing from the spirit and the scope of the invention. The present application is based on a Japanese patent application filed on Feb. 28, 2020 (patent application No. 2020-033890), and the contents thereof are incorporated here by reference.

Although the invention has been explained in detail referring to specific embodiments, it is obvious to one skilled in the art that various changes and modifications can be made without departing from the spirit and the scope of the invention.

INDUSTRIAL APPLICABILITY

The fatty acid calcium salt particles of the invention have excellent use feeling such as smoothness, adhesion to the skin and transparency and thus are suitable as an additive for cosmetics such as foundation and eye shadow.

The invention claimed is:

1. A fatty acid calcium salt particle consisting of a calcium salt of a fatty acid having 12 to 22 carbon atoms, wherein the particle have a plate shape, the median size of the particle is 4.0 μm to 15.0 μm, the particle size digest A expressed by the following equation (1) satisfies the relation A≤2.0, and the average thickness is 350 to 800 nm:

$$\text{the particle size digest } A = (D90 - D10)/D50 \quad \text{equation (1)},$$

wherein $4.0 \leq D50 \leq 15.0$,
wherein D10 is the 10% cumulative size in μm of the fatty acid calcium salt particle on a volumetric basis,
D50 is the median size in μm of the fatty acid calcium salt particle on a volumetric basis, and
D90 is the 90% cumulative size in μm of the fatty acid calcium salt particle on a volumetric basis.

2. The fatty acid calcium salt particle according to claim 1, wherein the fatty acid having 12 to 22 carbon atoms is myristic acid.

3. A cosmetic containing the fatty acid calcium salt particle according to claim 1.

4. A cosmetic containing the fatty acid calcium salt particle according to claim 2.

5. The fatty acid calcium salt particle according to claim 1, wherein the median size of the particle is 4.0 to 10.0 μm, wherein the following relationship is satisfied $0.5 \leq A \leq 1.8$ and wherein the average thickness is 400 to 700 nm.

* * * * *